United States Patent [19]

Heikkiläet al.

[11] Patent Number: 5,611,346
[45] Date of Patent: Mar. 18, 1997

[54] METHOD OF INTERFERENCE-TOLERANT TRANSMISSION OF HEARTBEAT SIGNALS

[75] Inventors: Ilkka Heikkilä; Arto Pietilä, both of Oulu, Finland

[73] Assignee: Polar Electro OY, Kempele, Finland

[21] Appl. No.: 416,792

[22] PCT Filed: Aug. 15, 1994

[86] PCT No.: PCT/FI94/00353

§ 371 Date: Apr. 14, 1995

§ 102(e) Date: Apr. 14, 1995

[87] PCT Pub. No.: WO95/05578

PCT Pub. Date: Feb. 23, 1995

[30] Foreign Application Priority Data

Aug. 16, 1993 [FI] Finland ...................................... 933612

[51] Int. Cl.⁶ .............................. A61B 5/04; A61B 5/0402
[52] U.S. Cl. ................................................ 128/696; 128/903
[58] Field of Search ........................................... 128/695, 696, 128/903; 607/60

[56] References Cited

U.S. PATENT DOCUMENTS

| 4,625,733 | 12/1986 | Säynäjäkangas | 128/696 |
|---|---|---|---|
| 4,958,645 | 9/1990 | Cadell et al. | 128/671 |
| 5,036,869 | 8/1991 | Inahara | 128/696 |
| 5,127,404 | 7/1992 | Wyborny et al. | 128/903 |
| 5,137,022 | 8/1992 | Henry | 128/903 |
| 5,241,961 | 9/1993 | Henry | 128/903 |
| 5,400,794 | 3/1995 | Gorman | 128/696 |

FOREIGN PATENT DOCUMENTS 212083  5/1985  Australia .............................. 128/696

*Primary Examiner*—George Manuel
*Assistant Examiner*—Carl H. Layno
*Attorney, Agent, or Firm*—Hoffmann & Baron

[57] ABSTRACT

A method of interference-tolerant heartbeat measurement comprises the steps of measuring the person's heartbeat signal at a suitable part of the body and transmitting the signal by telemetric transmission from a transmitter to a receiver as a pulse message formed by successive measuring pulses. A transmission interval of at least some pulse signals is proportional to the person's measured heartbeat rate. Each measuring pulse is formed of at least two identification pulses (C1 and C2), whereby the time interval ($t_x$) between the identification pulses corresponds to a specific time interval determined for each transmitter-receiver pair, on the basis of which specific interval the receiver identifies the pulse signals intended for itself.

12 Claims, 2 Drawing Sheets

5,611,346

METHOD OF INTERFERENCE-TOLERANT TRANSMISSION OF HEARTBEAT SIGNALS

BACKGROUND OF THE INVENTION

This invention relates to a method of interference-tolerant heartbeat measurement, in which method a person's heartbeat signal is measured at a suitable part of the body and transmitted by telemetric transmission from a transmitter to a receiver as pulse data formed by successive measuring pulses, in which data a transmission interval of at least some pulse signals is proportional to the person's measured heartbeat rate.

Known telemetric transmitters of heartbeat measuring devices typically transmit a burst of about 5 kHz each time they detect an ECG signal. A transmitter circuit is constituted by a simple resonance circuit activated by transistor control. At heartbeat measurement, a transmitter unit sends a signal each time the heart beats. A receiver calculates the heartbeat rate on the basis of the difference of time between the successive signals transmitted, which means that the method in principle consists of time interval coding, i.e. that the data to be transmitted is included in the transmission and coded into the time between the pulses.

The known method described above is simple and reliable in conditions free of interference. Single interferences can be filtered off by comparing the obtained pulse value with preceding results: if a new measurement result differs too much from the preceding ones, it is obviously caused by some outer interference coupled to the transmission-reception channel and may thus be eliminated from the measurement results.

However, if wireless transmission of pulse data is performed in an interfered environment, the situation changes essentially. A continuous irregular pulse train may then arrive at the receiver, from which train to pick up the correct pulse signal is a difficult task, often even impossible. Such a situation arises easily when two or several users of pulsimeters are too close to each other.

SUMMARY OF THE INVENTION

The object of this invention is to provide methods by means of which the above-mentioned drawbacks are avoided and a coding of a pulse signal is effected in such a way that it is possible to pick up the correct signals from an incoming interfered signal flow reliably and accurately without deteriorating the original accuracy of the moment of timing the signal.

To achieve this, the method according to the invention is characterized in that each transmission of pulse data comprises at least two identification pulses, whereby the time interval between the identification pulses corresponds to a specific time interval determined for each transmitter-receiver pair, on the basis of which specific interval the receiver identifies the measuring pulses intended for itself.

By means of the method of the invention, it is possible to pick up the correct pulse data from the incoming interfered signal flow reliably and accurately without deteriorating the original accuracy of the moment of timing the signal carrying the pulse measuring information.

Preferred embodiments of the invention are characterized in what is disclosed below in the attached claims.

In the following the invention will be described in greater detail by means of embodiments with reference to the attached drawings, in which

DETAILED DESCRIPTION OF THE INVENTION

Figure 1:
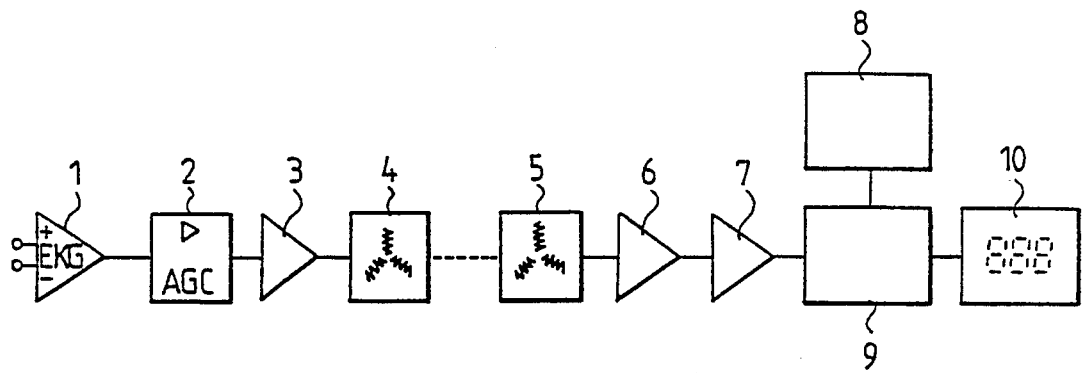
FIG. 1 shows a block diagram of a known telemetric heartbeat measuring device, to which the method according to the invention can be applied.
Figure 2:
FIG. 2 illustrates schematically a burst signal applied to magnetic coils of a transmitter according to FIG. 1.

Electrodes (not shown) of a telemetric heartbeat measuring device shown in FIG. 1 are connected to differential input terminals of an ECG preamplifier. A pulse signal given by the preamplifier 1 is amplified in an AGC amplifier 2, by which a power amplifier 3 is controlled, which generates an ac signal according to FIG. 2, i.e. a burst signal, controlling coils 4. A magnetic field detected by receiver coils 5 is amplified in a sensitive preamplifier 6, and then the signal is applied to a signal amplifier 7. An output signal of the signal amplifier is processed in a microcomputer 8, which stores the pulse data calculated at the measuring stage in a memory 9 and displays them on a liquid crystal display 10.

In practice, transmitter electronics transmits a burst of about 5 ms. The receiver repeats the burst substantially equal in duration. However, the receiver circuit requires after the burst a recovery time, during which it is not capable of separating a new transmission burst from the previous one. Experiments have shown that this time varies between 10 and 20 ms. On account of this, the present pulsimeters cannot use a pulse interval shorter than 20 ms, and thus, such an interval cannot be included in the coding according to the invention.

A coding of identification and pulse data can start from a basic period of about 1 ms, corresponding to the shortest detectable difference of an identification code based on time interval. To this coded data is added 25 ms, so that the shortest possible pulse interval will be sufficiently separated from a break pulse period.

If necessary, devices requiring shorter recovery times may be developed, whereby the time available and thus the number of identification codes may be increased.

Hereafter, the word message signifies a group of pulses, containing separate or combined identification pulses and heartbeat data pulses. Accordingly, message pulse is a common name for all pulses included in a transmission.

Figure 3:
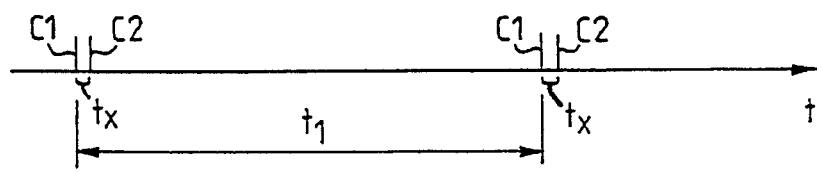
FIG. 3 illustrates an embodiment of the method of coding pulse data according to the invention.

One embodiment of the method of the invention appears from FIG. 3, in which a coding of pulse data into a time interval $t_1$ is implemented by using a double pulse, whereby a person's measured heartbeat rate is proportional to the transmission interval $t_1$ of double pulse signals. In a coding method of FIG. 3, two message pulses C1 and C2 separated by a fixed time interval $t_x$ are used instead of a single measuring pulse. The fixed time interval $t_x$ between these message pulses C1, C2 is interpreted, according to the invention, as an identification code of said transmission and the time interval between two such message pairs as the pulse data to be transmitted. By means of the procedure according to this embodiment, it is possible to separate almost all interfering messages from the correct signal.

However, if an interfering signal arrives at the receiver at a moment which is at a distance of the used code from the correct message pair, before or after, it is impossible to pick up the correct message from a pulse train having equal intervals. Such a coverage situation is usual when simultaneous transmissions of two transmitters close to each other mix with each other. The signals overlap each other at certain intervals, depending on the mutual difference between the time intervals of the message pulses, i.e. the codes of the pulse data. The closer these time intervals are to each other, the more seldom they cover each other—bug the longer at a time. On the other hand, if the difference between the time intervals is great, the message pulses coincide probably only at one of the successive transmissions, but overlaps succeed each other more often.

Due to the overlap phenomena, it is, however, impossible to separate transmissions completely reliably by using double pulse technique, but this technique is applicable to measuring devices intended for amateurs, for instance, whereby a less critical view can be taken of the correctness of each meter reading, when the meter is used in the vicinity of other meters.

Figure 4:
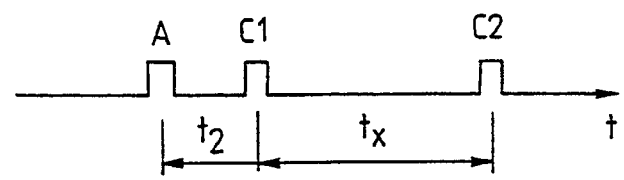
FIG. 4 illustrates another embodiment of the method of coding pulse data according to the invention.

FIG. 4 illustrates the principle of another embodiment of the invention, using triple pulse coding for separating pulse messages from each other. At triple pulse coding, one break pulse is added with respect to the method of FIG. 2 before actual message pulses transmitting an identification code. A break pulse A is transmitted during a fixed, very short (20 ms) time interval $t_2$ before identification pulses C1 and C2.

In the receiver, the break pulse is at first searched for: initially, each incoming pulse is assumed to be a break pulse. If the following transmission is received during a correct time interval (20 ms), the latter identification pulse is expected next. If the next pulse arrives at the right time, the pulse data is transmitted further to a calculation logic for determining the pulse rate value.

If interferences mix into the transmission channel, they can in this case arrive at the receiver either before the break pulse, between the break pulse and the first identification pulse, or between the identification pulses.

An interference arriving before the break pulse A causes a problematic situation only if it arrives just at the break time (20 ms) before the break pulse. In this case two pieces of information in length of the break pulse interval arrive at the identification logic. The correct message is then separated by means of the two identification pulses: an identification sequence started upon a first interfering pulse is interrupted by an error situation at the first identification pulse. A new correct sequence can then be started upon the genuine break pulse—this presupposes naturally that the arriving pulses are stored for a later change of the starting moment of the sequence.

An interfering pulse occurring between the break pulse A and the first identification pulse C1 may also interfere an already started identification sequence. The time interval and timing of the two original break pulses may, however, be restored by adding together the two time intervals shorter than the known break pulse interval.

An interference occurring between the identification pulses C1 and C2 changes the code of the message pulses into a wrong code. A wrongly timed pulse coming at this stage can be ignored, and concentration can be focussed on expecting the next, correct identification pulse C2. If such a pulse comes at the right moment, the receiver operates normally. Otherwise, the transmission is interpreted as erroneous.

Figure 5:
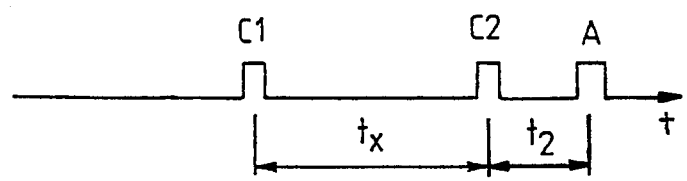
FIG. 5 illustrates a third embodiment of the method of coding pulse data according to the invention.

As a variation of the coding according to FIG. 4, the pulse data may be formed according to FIG. 5 by transmitting at first the first and the second identification pulse C1 and C2, the time interval $t_x$ of which still corresponds to the specific time interval of the transmitter-receiver. Not until then a break pulse A is transmitted after a fixed time interval $t_2$. In this case, the identification pulses are at first searched for in the receiver. The transmission intervals of the identification pulses may be measured e.g. continuously, irrespective of whether the pulse data is intended for said receiver or not. When the time interval between the identification pulses indicates that the pulse data is intended for said receiver, the break pulse is expected, and if it is received after the correct time interval $t_2$ (20 ms), the pulse data is transmitted further to the calculation logic for determining the pulse rate value. The examination of interference situations set forth in connection with the embodiment of FIG. 4 is applicable to the solution of FIG. 5.

Nearly all interference situations which are due to a simultaneous use of two transmitters having different identification data may be derived from the above-described situations caused by one interfering pulse. However, there is a small theoretical possibility that a single interfering pulse is switched on a transmission having a longer interval between the identification pulses in such a way that the entity also may be interpreted as a transmission containing shorter identification. This is also true vice versa, which means that, after a shorter identification field, one interference arriving exactly at the right moment may cause the same identification problem. The situation is, however, very unlikely and, accordingly, it does not restrict the use of the coding method according to the invention for a reliable pulse measurement also under demanding conditions.

On the basis of the above, it has been empirically found out that a completely reliable transmission and reception of simultaneous pulse data on two or several channels require:

transmission of a break pulse A;

transmission of two identification pulses C1 and C2; and storage of at least 6 successive pulse intervals in a buffer of the receiver for separating simultaneous transmissions.

Figure 6:
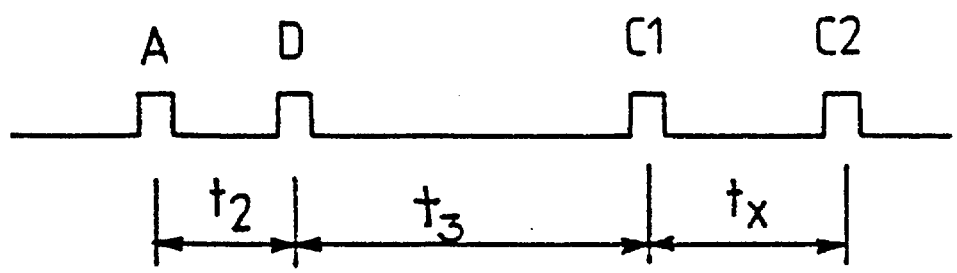
FIG. 6 illustrates the principle of a fourth embodiment of the invention.

The method according to the invention may also be easily applied to coding pulse data into the message pulses. In that case the pulse data to be transmitted, coded into a pulse interval, is inserted according to FIG. 6 between a break pulse A and identification pulses C1, C2 e.g. in such a way that, subsequent to the break pulse A, a first measuring pulse D of the pulse data is transmitted after a fixed time interval $t_2$ and then, after a time interval $t_3$ proportional to the pulse rate data, a second measuring pulse is transmitted, which simultaneously is the first identification pulse C1. Subsequently, a second identification pulse C2 is transmitted, the time interval $t_x$ between these identification pulses being equal to the specific time interval determined for said transmitter-receiver, as described earlier.

Since the pulse data in this case is included in the message pulses, the time between successive transmissions does not necessarily contain any information. To minimize the probability of interference situations caused by overlap phenomenon, the transmission interval of the message pulses can, according to one embodiment of the invention, be set to be randomly variable. Experiments have shown that a working transmission interval is an interval in which the time between transmissions ($t_1$ in FIG. 3) varies randomly between 2 and 4 seconds. Random time contributes considerably to the purpose of separating several transmissions faultlessly.

On the other hand, the transmission can be made safer according to another embodiment of the invention by including the pulse data both in the message pulses and in the time between the transmissions, through which a transmission coding as reliable and tolerant of interference as possible is provided.

According to still one embodiment of the invention, the message pulses may contain e.g. a consecutive number or some other identification, on the basis of which the receiver may discover the missing or extra transmissions. By using a configuration of a four-pulse message according to FIG. 6, the time interval $t_3$ between the pulse after the break pulse and the subsequent pulse may also be used for this purpose. In the following, reference is made to FIG. 6 by using the same reference numerals. To begin with, a break pulse A is transmitted, as described above. Then after a fixed time interval, a first identification pulse D is transmitted, and subsequently, after the time interval $t_3$ proportional to the consecutive number or the like of the transmission, a second identification pulse C1 is transmitted. After that a third identification pulse C2 is transmitted, the time interval between the second and third identification pulses being equal to the specific time interval determined for said transmitter-receiver.

The specific time interval of a transmitter-receiver may be fixed or it may preferably also be formed when starting the transmitter by a random operation, to which the receiver is locked for the time of the measuring procedure. The starting takes place e.g. by taking the receiver close to the transmitter, due to which the high level of a received signal starts the measurement, for instance in the way presented in the Finnish Patent 88972 of the applicant.

It is clear to one skilled in the art that the different embodiments of the invention are not restricted to the examples shown, but that they can vary within the scope of the claims below. The scope of the invention thus also allows a use of pulse transmissions which are more complicated than the examples shown and combine, for instance, the functions of two or several embodiments described here. However, the only essential thing is that the time interval between the two identification pulses contained in the transmission corresponds to the specific time interval determined for each transmitter-receiver.

What is claimed:

1. Method of interference-tolerant heartbeat measurement, said method comprising the steps of:
   (a) measuring a person's heartbeat signal at a suitable part of said person's body;
   (b) forming groups of data pulses corresponding to measurements of said heartbeat signal, each of said groups of data pulses including at least first and second identification pulses separated by a first time interval, said first time interval being selected for identification of a transmitter-receiver pair including a transmitter and a receiver;
   (c) transmitting said groups of data pulses from said transmitter to said receiver by telemetric transmission said groups of data pulses including at least some pulse signals which are separated by a second time interval, said second time interval being proportional to a heartbeat rate corresponding to said person's measured heartbeat signal;
   (d) receiving said groups of data pulses in said receiver; and
   (e) identifying said groups of data pulses as emanating from said transmitter by means of sensing said first time interval between said first and second identification pulses.

2. Method according to claim 1, wherein:
   in step (b), said groups of data pulses include a break pulse followed after a third time interval by the first identification pulse; and
   in step (c), break pulses of sucessive groups of said data pulses are separated by said second time interval.

3. Method according to claim 1, wherein:
   in steb (b), said groups of data pulses include a break pulse which follows a third time interval after said second identification pulse; and
   in step (c), first identification pulses of successive groups of said data pulses are separated by said second time interval.

4. A method in accordance with claim 1, wherein in said transmitting step, said telemetric transmission comprises transmission by magnetic inductive coupling.

5. Method according to claim 1, wherein in step (b), said groups of data pulses include:
   a break pulse;
   a first measuring pulse following a third time interval after said break pulse; and
   a second measuring pulse, which simultaneously is the first identification pulse, following said second time interval after said first measuring pulse.

6. Method according to claim 5, wherein step (c) includes the sub-step of separating said groups of data pulses by a transmission interval which is set to be randomly variable in such a way that the time between the groups of data pulses varies randomly within predetermined limits.

7. A method in accordance with claim 6, wherein said predetermined limits are between 2 and 4 seconds.

8. Method of interference-tolerant heartbeat measurement, said method comprising the steps of:
   (a) measuring a person's heartbeat signal at a suitable part of said person's body;
   (b) forming first and second groups of pulses corresponding to at least first and second measurements of said heartbeat signal, each of said groups of pulses including:
      (i) a first pulse, said first pulse being a break pulse;
      (ii) a second pulse, said second pulse being a measuring pulse, said second pulse following a first time interval after said first pulse, said first time interval being fixed;
      (iii) a third pulse, said third pulse being both a measuring pulse and an identification pulse, said third pulse following a second time interval after said second pulse, said second time interval being variable and being proportional to a heartbeat rate corresponding to said person's measured heartbeat signal; and
      (iv) a fourth pulse, said fourth pulse being an identification pulse, said fourth pulse following a third time interval after said third pulse, said third time interval being fixed and being equal to a specific time interval preselected for identification of a transmitter-receiver pair including a transmitter and a receiver;
   (c) transmitting said first and second groups of pulses from said transmitter to said receiver by telemetric transmission, said first and second groups of pulses being separated by a fourth time interval, said fourth time interval being proportional to said heartbeat rate corresponding to said person's measured heartbeat signal;

(d) receiving said first and second groups of pulses in said receiver; and (e) identifying said first and second groups of pulses as emanating from said transmitter by means of sensing said third time interval between said third and fourth pulses of each of said first and second groups of pulses.

9. Method of interference-tolerant heartbeat measurement, said method comprising the steps of:

(a) measuring a person's heartbeat signal at a suitable part of said person's body;

(b) forming groups of pulses corresponding to measurements of said heartbeat signal, each of said groups of pulses including:
  (i) first pulse, said first pulse being a break pulse;
  (ii) a second pulse, said second pulse being a first identification pulse, said second pulse following a first time interval after said first pulse;
  (iii) a third pulse, said third pulse being a second identification pulse, said third pulse following a second time interval after said second pulse, said second time interval being proportional to a consecutive transmission number or the like; and
  (iv) a fourth pulse, said fourth pulse being a third identification pulse, said fourth pulse following a third time interval after said third pulse, said third time interval being equal to a specific time interval selected for identification of a transmitter-receiver pair including a transmitter and a receiver;

(c) transmitting said groups of pulses from said transmitter to said receiver by telemetric transmission, said groups of pulses being separated by a fourth time interval, said fourth time interval being proportional to a heartbeat rate corresponding to said person's measured heartbeat signal;

(d) receiving said groups of pulses in said receiver; and (e) identifying said groups of pulses as emanating from said transmitter by means of sensing said third time interval between said third and fourth pulses of each of said groups of pulses.

10. Method of interference-tolerant heartbeat measurement, said method comprising the steps of:

(a) measuring a person's heartbeat signal at a suitable part of said person's body;

(b) forming a first specific time interval for a transmitter-receiver pair including a transmitter and a receiver, said first specific time interval of said transmitter-receiver pair being formed by a random operation when said transmitter is started, said receiver being locked to said first specific time interval throughout a time for which said person's heartbeat is to be measured for purposes of identifying said transmitter to said receiver;

(c) subsequent to step (b), forming first and second groups of pulses corresponding to at least first and second measurements of said heartbeat signal, each of said groups of pulses including at least first and second identification pulses separated by said first time interval;

(d) transmitting said first and second groups of pulses from said transmitter to said receiver by telemetric transmission, said first and second groups of pulses being separated by a second time interval, at least one of:
  (i) said second time interval; and
  (ii) a third time interval between pulses within said first and second groups of pulses being proportional to a heartbeat rate corresponding to said person's measured heartbeat signal;

(e) receiving said first and second groups of pulses in said receiver; and (f) identifying said first and second groups of pulses as emanating from said transmitter by means of sensing said first specific time interval between said first and second identification pulses of each of said first and second groups of pulses.

11. Method of interference-tolerant heartbeat measurement, said method comprising the steps of:

(a) measuring a person's heartbeat signal at a suitable part of said person's body;

(b) forming first and second groups of pulses corresponding to at least first and second measurements of said heartbeat signal, each of said groups of pulses including at least first and second identification pulses separated by a first specific time interval, said first specific time interval being preselected for time-interval-coded identification of a transmitter-receiver pair including a transmitter and a receiver;

(c) transmitting said first and second groups of pulses from said transmitter to said receiver by telemetric transmission, said first and second groups of pulses being separated by a second time interval, at least one of:
  (i) said second time interval; and
  (ii) a third time interval between pulses within each of said first and second groups of pulses being proportional to a heartbeat rate corresponding to said person's measured heartbeat signal and constituting a time-interval-coded representation of said heartbeat rate;

(d) receiving said first and second groups of pulses in said receiver; and (e) identifying said first and second groups of pulses as emanating from said transmitter by means of sensing said first specific time interval between said first and second identification pulses of each of said first and second groups of pulses.

12. A method in accordance with claim 11, wherein in said transmitting step, said telemetric transmission comprises transmission by magnetic inductive coupling.

* * * * *

(12) EX PARTE REEXAMINATION CERTIFICATE (10313th)
United States Patent
Heikkilä et al.

(10) Number: US 5,611,346 C1
(45) Certificate Issued: Oct. 8, 2014

(54) METHOD OF INTERFERENCE-TOLERANT TRANSMISSION OF HEARTBEAT SIGNALS

(75) Inventors: Ilkka Heikkilä, Oulu (FI); Arto Pietilä, Oulu (FI)

(73) Assignee: Polar Electro OY, Kempele (FI)

Reexamination Request:
No. 90/012,929, Jul. 26, 2013

Reexamination Certificate for:
Patent No.: 5,611,346
Issued: Mar. 18, 1997
Appl. No.: 08/416,792
Filed: Apr. 14, 1995

(21) Appl. No.: 90/012,929

(22) PCT Filed: Aug. 15, 1994

(86) PCT No.: PCT/FI94/00353
§ 371 (c)(1),
(2), (4) Date: Apr. 14, 1995

(87) PCT Pub. No.: WO95/05578
PCT Pub. Date: Feb. 23, 1995

(30) Foreign Application Priority Data

Aug. 16, 1993 (FI) .......................................... 933612

(51) Int. Cl.
*A61B 5/00* (2006.01)
*A61B 1/00* (2006.01)

(52) U.S. Cl.
USPC .......................... 600/509; 128/903; 600/523

(58) Field of Classification Search
None
See application file for complete search history.

(56) References Cited

To view the complete listing of prior art documents cited during the proceeding for Reexamination Control Number 90/012,929, please refer to the USPTO's public Patent Application Information Retrieval (PAIR) system under the Display References tab.

*Primary Examiner* — Sam Rimell

(57) ABSTRACT

A method of interference-tolerant heartbeat measurement comprises the steps of measuring the person's heartbeat signal at a suitable part of the body and transmitting the signal by telemetric transmission from a transmitter to a receiver as a pulse message formed by successive measuring pulses. A transmission interval of at least some pulse signals is proportional to the person's measured heartbeat rate. Each measuring pulse is formed of at least two identification pulses (C1 and C2), whereby the time interval ($t_x$) between the identification pulses corresponds to a specific time interval determined for each transmitter-receiver pair, on the basis of which specific interval the receiver identifies the pulse signals intended for itself.

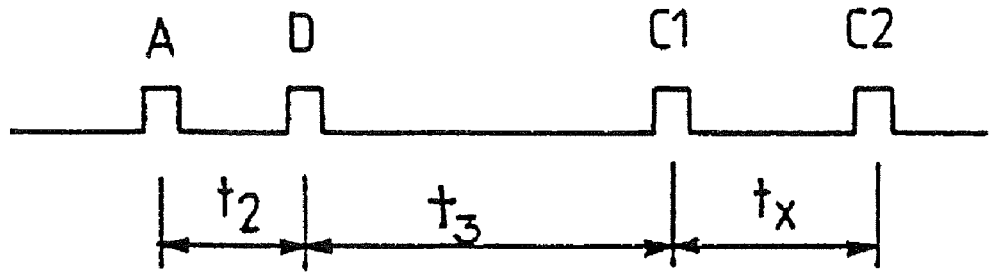

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-12 is confirmed.

\* \* \* \* \*